(12) United States Patent
Marshall et al.

(10) Patent No.: US 12,115,096 B2
(45) Date of Patent: Oct. 15, 2024

(54) PATIENT POSITIONING SYSTEM

(71) Applicant: KPR U.S., LLC, Mansfield, MA (US)

(72) Inventors: Stephen Marshall, Cataumet, MA (US); Byron Wesley Kerns, Franklin, MA (US)

(73) Assignee: KPR U.S., LLC, Mansfield, MA (US)

( * ) Notice: Subject to any disclaimer, the term of this patent is extended or adjusted under 35 U.S.C. 154(b) by 249 days.

(21) Appl. No.: 17/688,223

(22) Filed: Mar. 7, 2022

(65) Prior Publication Data

US 2022/0183874 A1    Jun. 16, 2022

Related U.S. Application Data

(63) Continuation of application No. 16/422,578, filed on May 24, 2019, now abandoned, which is a
(Continued)

(51) Int. Cl.
*A61F 5/37*        (2006.01)
*A47C 20/02*       (2006.01)
(Continued)

(52) U.S. Cl.
CPC ............ *A61F 5/3776* (2013.01); *A61G 1/044* (2013.01); *A61G 7/065* (2013.01); *A61G 13/12* (2013.01);
(Continued)

(58) Field of Classification Search
CPC ........ A61F 5/3776; A61F 5/3769; A61F 5/37; A61F 5/01; A61F 5/3723; A61F 5/3715; A61F 2013/5688; A61G 13/122; A61G 13/1235; A61G 13/121; A61G 13/12; A61G 7/065; A61G 13/0036; A61G 13/00; A61G 13/1215; A61G 13/1225; A61G 1/044;
(Continued)

(56) References Cited

U.S. PATENT DOCUMENTS 2,099,977 A  11/1937  Harris
2,182,861 A  12/1939  Albert
(Continued)

FOREIGN PATENT DOCUMENTS

DE  202007016952 U1  4/2009
EP       0731114 A1  9/1996
(Continued)

OTHER PUBLICATIONS

"Sheet." Vocabulary, www.vocabulary.com/dictionary/sheet.*
(Continued)

*Primary Examiner* — Justin C Mikowski
*Assistant Examiner* — Madison Emanski
(74) *Attorney, Agent, or Firm* — ArentFox Schiff LLP

(57) ABSTRACT

A system and method are disclosed for positioning a patient on an operating table. The patient positioning system includes a positioning pad having a body formed from a compressible material including a slip-resistant surface. The body has a thickness which increases from a first end of the positioning pad to a second end of the positioning pad. A plurality of tethers are fixedly secured to the body. Each of the tethers includes a fastening member adapted to secure the body to an operating table.

11 Claims, 7 Drawing Sheets

Related U.S. Application Data continuation of application No. 15/133,566, filed on Apr. 20, 2016, now abandoned, which is a continuation of application No. 14/228,962, filed on Mar. 28, 2014, now Pat. No. 9,375,343.

(60) Provisional application No. 61/927,019, filed on Jan. 14, 2014, provisional application No. 61/902,447, filed on Nov. 11, 2013, provisional application No. 61/900,036, filed on Nov. 5, 2013, provisional application No. 61/836,465, filed on Jun. 18, 2013.

(51) Int. Cl.
- *A61G 1/044* (2006.01)
- *A61G 7/065* (2006.01)
- *A61G 13/12* (2006.01)

(52) U.S. Cl.
CPC ........ *A61G 13/121* (2013.01); *A61G 13/122* (2013.01); *A61G 13/1225* (2013.01); *A61G 13/123* (2013.01); *A61G 13/1235* (2013.01); *A47C 20/027* (2013.01); *A61F 5/37* (2013.01)

(58) Field of Classification Search
CPC .............. A61G 7/0504; A61G 13/0054; A61G 7/05715; A61B 6/0421; Y10S 5/922; A47D 15/005; A47D 13/08; A47G 9/04
USPC ... 5/623, 628, 621, 647, 655, 424, 633, 922, 5/632, 942, 622, 6, 32; 128/845, 870, 128/876; 297/377; 604/385.01
See application file for complete search history.

(56) References Cited

U.S. PATENT DOCUMENTS

| | | |
|---|---|---|
| 3,539,577 A | 11/1970 | Martin et al. |
| 3,648,308 A | 3/1972 | Greenawalt et al. |
| 3,650,523 A | 3/1972 | Charles |
| 3,729,752 A | 1/1973 | Huggins |
| 3,721,434 A | 3/1973 | Spies |
| 3,817,509 A | 6/1974 | Komline |
| 3,946,451 A | 3/1976 | Spann |
| 4,034,972 A | 7/1977 | Peterson |
| 4,066,072 A | 1/1978 | Cummins |
| 4,132,228 A | 1/1979 | Green |
| 4,193,150 A | 3/1980 | Vineberg |
| 4,206,524 A | 6/1980 | Cook |
| 4,392,489 A | 7/1983 | Wagner |
| 4,397,052 A | 8/1983 | Lund, III |
| 4,398,707 A * | 8/1983 | Cloward ................ A61G 13/12 5/632 |
| 4,501,414 A | 2/1985 | Mason et al. |
| 4,601,075 A | 7/1986 | Smith |
| 4,678,171 A | 7/1987 | Sanders et al. |
| 4,742,821 A | 5/1988 | Wootan |
| 4,802,249 A | 2/1989 | Bills |
| 4,905,330 A | 3/1990 | Jacobs |
| 4,907,306 A | 3/1990 | Nakaji |
| 4,947,500 A | 4/1990 | Seiler |
| 4,944,053 A | 7/1990 | Smith |
| 4,964,400 A | 10/1990 | Laico et al. |
| 5,079,790 A | 1/1992 | Pouch |
| 5,095,569 A | 3/1992 | Glenn |
| 5,163,194 A * | 11/1992 | Dixon ................... A47G 9/1081 5/639 |
| 5,329,934 A | 7/1994 | Bowman |
| 5,394,577 A | 3/1995 | James et al. |
| 5,439,008 A | 8/1995 | Bowman |
| 5,448,790 A | 9/1995 | Saro et al. |
| 5,463,781 A | 11/1995 | Jones |
| 5,638,558 A | 6/1997 | Moore |
| 5,657,766 A | 8/1997 | Durham |
| 5,669,094 A | 9/1997 | Swanson |
| D387,167 S | 12/1997 | Klein et al. |
| 5,697,112 A | 12/1997 | Colavito et al. |
| 5,762,073 A | 6/1998 | Choy |
| 5,771,515 A | 6/1998 | Carr |
| 5,987,675 A | 11/1999 | Kim |
| 6,001,076 A | 12/1999 | Wilson et al. |
| 6,009,873 A | 1/2000 | Neviaser |
| 6,049,927 A | 4/2000 | Thomas et al. |
| 6,052,851 A | 4/2000 | Kohnle |
| 6,159,574 A | 12/2000 | Landvik et al. |
| 6,182,316 B1 | 2/2001 | Thomas et al. |
| 6,292,964 B1 | 9/2001 | Rose et al. |
| 6,308,353 B1 | 10/2001 | Van |
| 6,360,387 B1 | 3/2002 | Everhart |
| 6,401,283 B2 | 6/2002 | Thomas et al. |
| 6,467,486 B1 | 10/2002 | Kleinschmidt |
| 6,516,483 B1 | 2/2003 | Vansteenburg |
| 6,553,995 B1 | 4/2003 | Cole et al. |
| 6,564,801 B1 | 5/2003 | Frank |
| 6,678,908 B2 | 1/2004 | Borders et al. |
| 6,725,481 B1 | 4/2004 | Marshall |
| 6,728,978 B1 | 5/2004 | Nordin |
| 6,735,798 B1 | 5/2004 | Sekizawa |
| 6,817,363 B2 | 11/2004 | Biondo et al. |
| 6,823,545 B1 | 11/2004 | Davis |
| 6,895,614 B1 | 5/2005 | Peck |
| 6,921,372 B2 | 7/2005 | Shin |
| 6,922,861 B1 | 8/2005 | Mathis |
| 6,925,670 B2 | 8/2005 | Torrez |
| 6,931,683 B1 | 8/2005 | Elkin et al. |
| 7,003,831 B1 | 2/2006 | Goutevenier-Reyher |
| 7,020,918 B1 | 4/2006 | Tinsley |
| 7,076,822 B2 | 7/2006 | Pearce |
| 7,107,639 B2 | 9/2006 | Taricani et al. |
| 7,251,846 B1 | 8/2007 | Elkin et al. |
| 7,287,289 B1 | 10/2007 | Hagopian |
| 7,328,471 B1 | 2/2008 | Stohr |
| 7,334,279 B2 | 2/2008 | Oprandi |
| 7,469,437 B2 | 12/2008 | Mikkelsen et al. |
| 7,536,740 B1 | 5/2009 | Swartz |
| 7,552,493 B2 | 6/2009 | McNulty et al. |
| 7,697,971 B1 | 4/2010 | Green et al. |
| 7,707,670 B2 | 5/2010 | Fogg |
| 7,784,129 B2 | 8/2010 | Javaruski et al. |
| 7,886,379 B2 | 2/2011 | Benzo et al. |
| 7,966,679 B2 | 6/2011 | Sakata et al. |
| 8,156,941 B1 | 4/2012 | Simms |
| 8,176,585 B1 | 5/2012 | Isham |
| D665,912 S | 8/2012 | Skripps |
| 8,272,089 B1 | 9/2012 | Stokes |
| 8,464,720 B1 | 6/2013 | Pigazzi et al. |
| 8,511,314 B2 | 8/2013 | Pigazzi et al. |
| 8,539,622 B2 | 9/2013 | West |
| 8,572,782 B1 | 11/2013 | Amini |
| 9,375,343 B2 | 6/2016 | Marshall et al. |
| 2003/0066134 A1 | 4/2003 | Chapman |
| 2003/0175473 A1 | 9/2003 | Gillum et al. |
| 2005/0034239 A1 | 2/2005 | Mann |
| 2005/0084667 A1 | 4/2005 | Landvik et al. |
| 2005/0172408 A1 | 8/2005 | Temple |
| 2006/0096031 A1 | 5/2006 | Foster |
| 2007/0056096 A1 | 3/2007 | Assink |
| 2008/0178390 A1 | 7/2008 | Dudonis |
| 2009/0004452 A1 | 1/2009 | Assink |
| 2010/0071131 A1 | 3/2010 | Gunkel et al. |
| 2010/0132119 A1 | 6/2010 | Taghijhani |
| 2010/0275377 A1 | 11/2010 | West |
| 2011/0047706 A1 | 3/2011 | Hiebert |
| 2011/0126355 A1 | 6/2011 | Hiebert |
| 2011/0179572 A1* | 7/2011 | Mohr ..................... A61G 1/044 5/628 |
| 2011/0191960 A1 | 8/2011 | Hiebert |
| 2012/0124742 A1 | 5/2012 | Soto et al. |
| 2012/0186587 A1* | 7/2012 | Steffens ................ A61G 7/001 128/845 |
| 2012/0247483 A1 | 10/2012 | Fylnn |
| 2012/0255124 A1 | 10/2012 | West |
| 2012/0272451 A1 | 11/2012 | Haskell et al. |
| 2013/0074264 A1 | 3/2013 | Shah et al. |

(56) References Cited

U.S. PATENT DOCUMENTS

| | | |
|---|---|---|
| 2013/0152950 A1 | 6/2013 | Giap |
| 2013/0167300 A1 | 7/2013 | Hammond |
| 2013/0289150 A1 | 10/2013 | Hager et al. |
| 2013/0312189 A1 | 11/2013 | Sarma et al. |
| 2013/0312772 A1 | 11/2013 | Carrier |
| 2014/0034062 A1 | 2/2014 | Pigazzi et al. |
| 2014/0173827 A1 | 6/2014 | Hiebert |

FOREIGN PATENT DOCUMENTS

| | | |
|---|---|---|
| EP | 1264586 A2 | 12/2002 |
| GB | 2396119 A | 6/2004 |
| WO | 2006110671 A2 | 10/2006 |

OTHER PUBLICATIONS

"About." Merriam-Webster, www.merriam-webster.com/dictionary/about.*

Armstrong et al., "An Integrative Review of Pressure Relief in Surgical Patients," Aorn Journal, Mar. 2001, vol. 73(3), pp. 645-674.

Dictionary. com, Definition of "to", 2019. Retrieved from the Internet:https://www.dictionary.com/browse/to.

Feuchtinger J et al., "A 4-cm Thermoactive Viscoelastic Foam Pad on the Operating Room Table to Prevent Pressure Ulcer During Cardiac Surgery," Journal of Clinical Nursing, Feb. 2006, vol. 15(2), pp. 162-167.

Gunningberg L et al., "Effect of visco-elastic foam mattress on the development of pressure ulcers in patients with hip fractures" Journal of Wound Care, Nov. 2000, vol. 9(10), pp. 455-459.

International Preliminary Report on Patentability dated Dec. 22, 2015, issued in PCT/US2014/042872.

International Search Report and Written Opinion for Application No. PCT/US2014/042872, mailed on Oct. 9, 2014, 9 pages.

Klauschie, MD, et al., "Use of Anti-Skid Material and Patient-Positioning to Prevent Patient Shifting During Robotic-Assisted Gynecologic Procecures", pp. 504-507.

Office Action dated Oct. 26, 2016 in related Canadian Application No. 2915263, 4 pages.

Russell L. J et al., "Randomized Clinical Trial Comparing 2 Support Surfaces: Results of the Prevention of Pressure Ulcers Study," Advances in Skin & Wound Care, Nov. 2003, vol. 16(6), pp. 317-327.

Wallace M "Review: Alternative-foam Mattresses and Some Operating-table Overlays Reduce Pressure Ulcers More Than Standard Surfaces," Evidence-based Nursing, Jul. 2009, vol. 12(3), pp. 1.

WWW.pressureulcerguidelines.org/prevention/files/Operating.sub.—Room. sub.—Statements.pdf, "Operating Room".

\* cited by examiner

PATIENT POSITIONING SYSTEM

CROSS-REFERENCE TO RELATED APPLICATIONS

The present Application for Patent is a Continuation of U.S. application Ser. No. 16/422,578, filed May 24, 2019, which a continuation of U.S. application Ser. No. 15/133,566, filed Apr. 20, 2016, which is a continuation of U.S. application Ser. No. 14/228,962, filed Mar. 28, 2014, which claims the benefit of and priority to U.S. Provisional Application Ser. No. 61/927,019, filed Jan. 14, 2014, U.S. Provisional Application Ser. No. 61/902,447, filed Nov. 11, 2013, U.S. Provisional Application Ser. No. 61/900,036, filed Nov. 5, 2013 and U.S. Provisional Application Ser. No. 61/836,465, filed Jun. 18, 2013, the entire contents of each of which is incorporated herein by reference.

BACKGROUND

1. Technical Field

The present disclosure relates to a system for securing a patient to an operating table. More specifically, the present disclosure relates to a system for immobilizing a patient on an operating table to perform a surgical procedure.

2. Background

In a variety of different surgical procedures, it is beneficial to place a patient in the Trendelenburg position. These procedures include gynecological, laparoscopic, abdominal, colorectal, urological and about 70% of robotic surgical procedures. In the Trendelenburg position, the patient is laid flat on the back (supine position) with the feet positioned higher than the head at an angle of between about fifteen degrees and about thirty degrees. In this position, gravity pulls the intestines away from the pelvis to allow a clinician better access to pelvic organs.

In the Trendelenburg position, the patient's body has a tendency to slide down the inclined operating table. A variety of products and methods are used to minimize patient slippage on the operating table. It would be desirable to provide an improved system for more securely positioning and immobilizing the patient on the operating table in the Trendelenburg and other positions.

SUMMARY

In accordance with one aspect of the present disclosure, a positioning pad is disclosed for positioning a patient on an operating table which comprises a body formed from a compressible material having a slip-resistant surface, a first end and a second end. The body has a thickness which increases from the first end of the positioning pad to the second end of the positioning pad. A plurality of tethers are provided on the positioning pad. Each of the tethers includes a fastening member adapted to secure the body to an operating table.

In some embodiments, the body includes a transverse cut which extends transversely from one side wall of the body to an opposite side wall of the body. The transverse cut is configured to allow placement of a sheet through and across the positioning pad in spaced relation to the slip-resistant surface.

In certain embodiments, the fastening member of each of the tethers includes hook and loop fasteners.

In some embodiments, the thickness of the pad at the first end is about one inch and the thickness of the pad at the second end is about three inches.

In certain embodiments, the transverse cut extends between the sidewalls of the positioning pad, is spaced from the first end of the positioning pad and extends through the second end of the positioning pad.

In another aspect of the disclosure, a patient positioning system is disclosed which includes a positioning pad having a body formed from a compressible material including a slip-resistant surface, a first end and a second end. The body has a thickness which increases from the first end of the positioning pad to the second end of the positioning pad. A plurality of tethers is fixedly secured to the body. Each of the tethers includes a fastening member adapted to secure the body to an operating table. The body includes a transverse cut which extends transversely from one side wall of the body to an opposite side wall of the body. The system also includes a sheet positioned within the transverse cut of the body of the positioning pad spaced from the slip-resistant surface of the positioning pad and at least one strap. The at least one strap has first and second ends adapted to be connected to an operating table and is dimensioned to extend across a patient to secure the patient to the operating table.

In an embodiment, the fastening member of each of the tethers includes hook and loop fasteners.

In certain embodiments, the thickness of the pad at the first end is about one inch and the thickness of the pad at the second end is about three inches.

In some embodiments, the transverse cut is spaced from the first end of the positioning pad and extends through the second end of the positioning pad.

In certain embodiments, the positioning system includes a head rest.

In some embodiments, the positioning system has at least one comfort strip dimensioned to be positioned between the at least one strap and a patient. The at least one strap can include two straps.

In certain embodiments, each strap includes a first strap half and a second strap half, wherein each strap half includes a first end adapted to engage an operating table and a second end adapted to engage the other strap half In yet another aspect of the disclosure, a method for positioning a patient on an operating table is disclosed which includes placing a compressible positioning pad on the operating table, the pad defining a transverse cut which extends from one side wall of the pad to an opposite side wall of the pad and including a sheet positioned through the transverse cut and extending from each side wall of the positioning pad; securing the pad to the operating table; positioning a patient on the pad in the supine position; securing the patient to the operating table using at least one strap; and wrapping the sheet around arms of the patient and tucking the ends of the sheet into the transverse cut.

In certain embodiments, the compressible pad has a thickness which increases from a first end wall of the positioning pad to a second end wall of the positioning pad and the step of positioning a patient on the pad includes positioning a head of a patient adjacent the second end wall of the positioning pad.

In some embodiments, the step of securing the patient to the operating table includes positioning the at least one strap over the chest of the patient and securing ends of the least one strap to the operating table.

In certain embodiments, the at least one strap includes two straps and the step of securing the patient to the operating table includes positioning the two straps over the patient in a diagonal configuration and securing the ends of each of the straps to the operating table.

In some embodiments, a perforated section is positioned adjacent the first end of the body and is configured to mirror a perineal cutout of an operating table.

In certain embodiments, the positioning pad is formed from first and second layers which are bonded together. The first and second layers may be formed from polyurethane foams.

BRIEF DESCRIPTION OF THE DRAWINGS

Various embodiments of the presently disclosed positioning system are described herein with reference to the drawings, wherein.

DETAILED DESCRIPTION OF EMBODIMENTS

Figure 1:
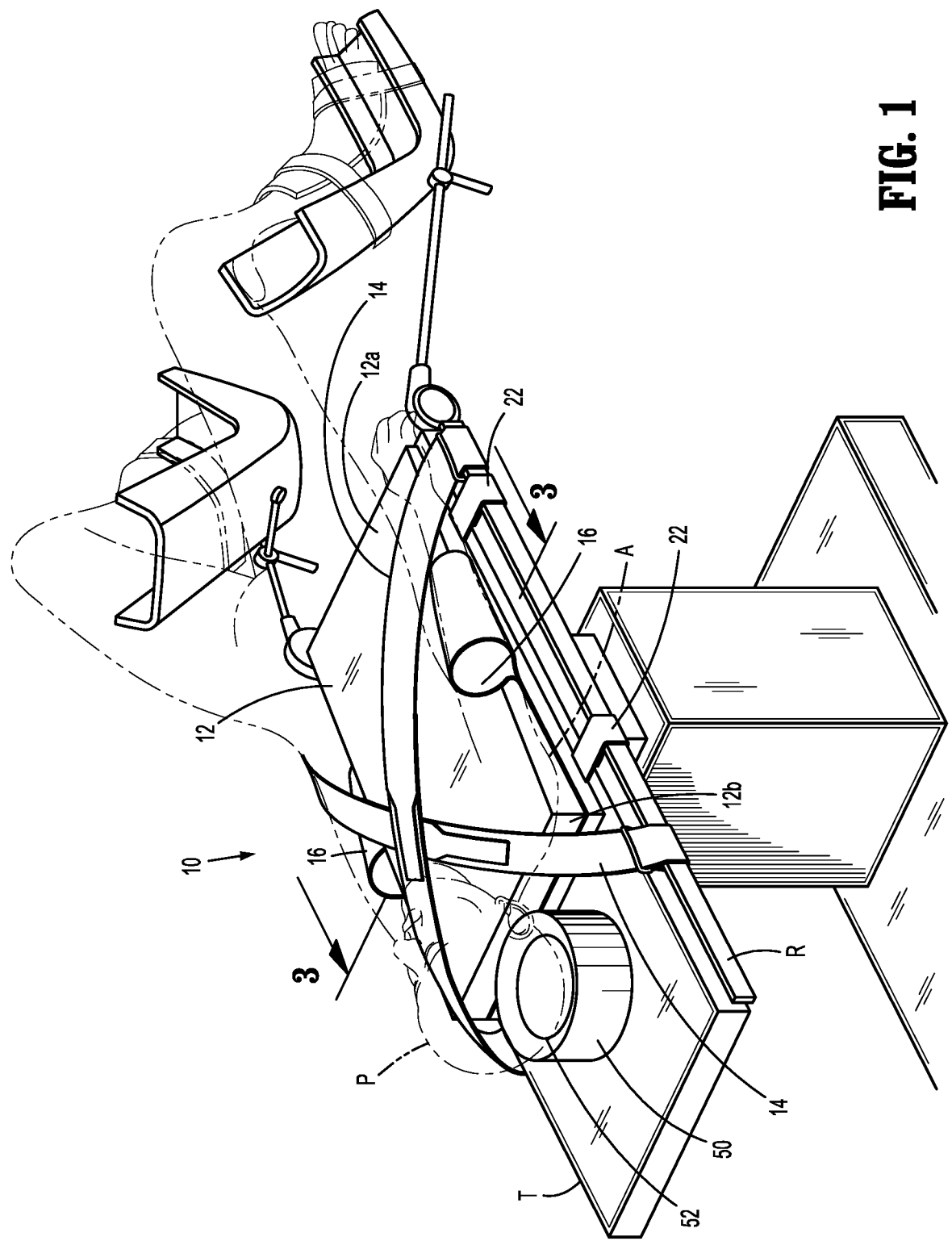
FIG. 1 is a side perspective view of an operating table with a patient shown in phantom secured to the table by the presently disclosed patient positioning system.

Referring to FIG. 1, the presently disclosed patient positioning system, shown generally as 10, includes a positioning pad 12, at least one strap 14 dimensioned to secure a patient P to an operating table T and a sheet 16. The positioning pad 12 is secured to the operating table T by a plurality of tethers 22. Each of the tethers 22 includes one or more fastening members 30 (FIG. 2), e.g., a buckle or hook and loop fasteners (e.g., Velcro), to facilitate securement of the tether 22 to the operating table T. In one embodiment, a pair of tethers 22 is secured to each end 12a and 12b of the positioning pad 12 by stitching or sewing. Alternately, the tethers 22 can be secured to the positioning pad 12 using other known fastening techniques.

As will be discussed in further detail below, the positioning pad 12 is secured to an operating table T with tethers 22 and a patient P is positioned onto the positioning pad 12. Thereafter, the patient P is secured to the operating table T using the straps 14. The positioning pad 12 is configured to better distribute a patient's weight onto an operating table T when the patient is positioned in an inclined position, e.g., the Trendelenburg position. The positioning pad 12 also is adapted to space the sheet 16 from the patient P to increase the surface area of the patient P which contacts the positioning pad 12 to better immobilize the patient as will be discussed in detail below.

Figure 2:
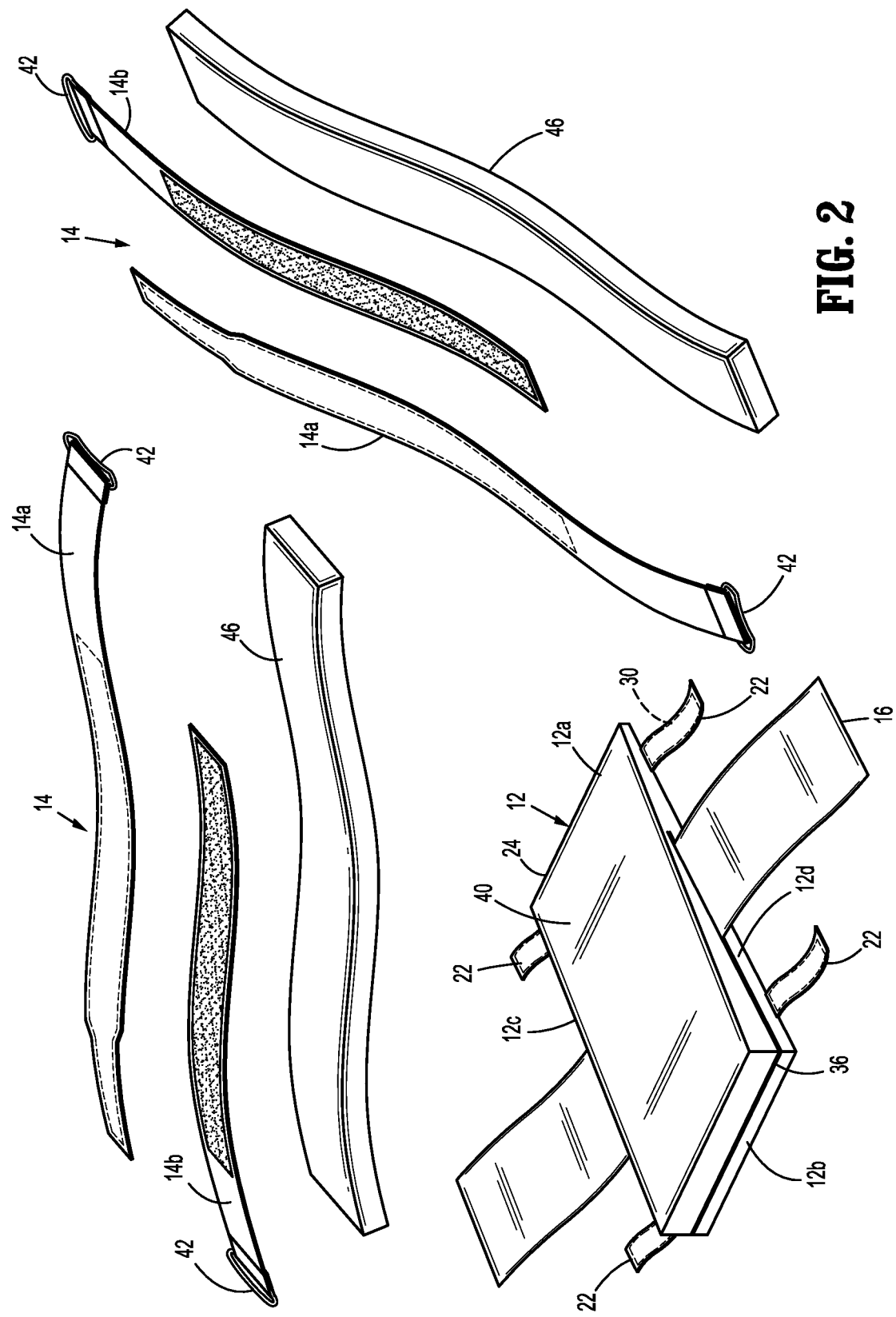
FIG. 2 is a side perspective view of the presently disclosed patient positioning system with a sheet positioned within a transverse cut of a positioning pad and remaining parts separated.
Figure 2A:
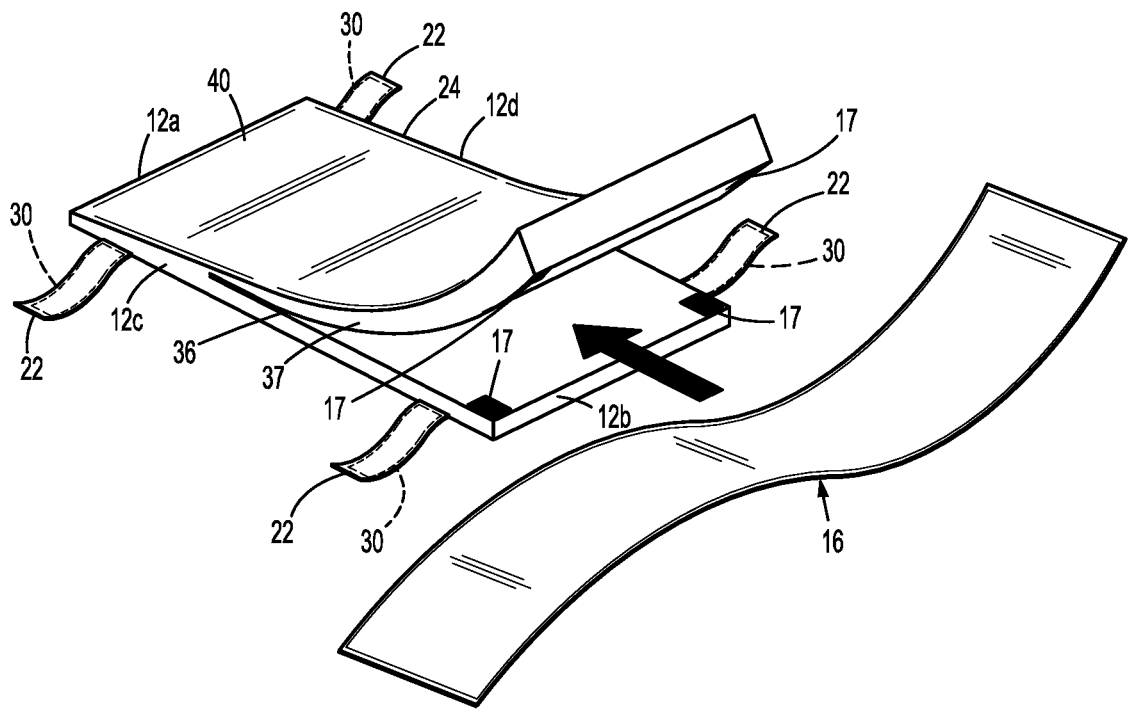
FIG. 2A is a side perspective view of the positioning pad and the sheet of the patient positioning system shown in FIG. 2 with a portion of the positioning pad deformed prior to the sheet being positioned within the transverse cut of the positioning pad.

Referring to FIGS. 2 and 2A, the positioning pad 12 includes a body 24 having a thickness which increases from a first end wall 12a of the positioning pad 12 to a second end wall 12b. In one embodiment, the thickness of the pad 12 increases uniformly over the length of the pad 12. Alternately, the pad 12 can have sections of uniform thickness or sections which have a thickness which increases at a faster or slower rate than other sections of the pad 12. The pad 12 is dimensioned to be thicker near the patient's head adjacent the shoulders where the highest amount of pressure is exerted to better redistribute the pressure exerted by the patient P onto the operating table T. In an embodiment, the positioning pad 12 increases in thickness from about one inch at the first end wall 12a to about three inches at the second end wall 12b. Alternatively, other pad thicknesses which may provide more desirable pressure distributions for certain surgical procedures are envisioned.

The positioning pad 12 is formed from a compressible foam material which defines a slip-resistant or tacky surface 40. The foam material can be a visco-elastic foam which conforms to the shape of a patient to minimize or prevent slippage of the patient in relation to the positioning pad 12. In one embodiment, the positioning pad 12 has a width of 20 inches and a length of 32 inches. Alternately, pads 12 having different dimensions to accommodate different size patients or which are more suitable for a specific surgical procedures are envisioned. The positioning pad 12 includes a transverse cut 36 that extends from one side wall 12c of the positioning pad 12 to the other side wall 12d of the positioning pad 12. The transverse cut 36 is dimensioned to receive the sheet 16 to provide separation between the sheet 16 and the patient. More specifically, the transverse cut 36 allows a portion of the positioning pad 12 to be deformed upwardly (FIG. 2A) to allow sheet 16 to pass beneath the patient P while allowing the patient's body to be in full contact with the slip-resistant pad surface 40. As such, a patient P (FIG. 1) can be more securely positioned on and immobilized in relation to the operating table T. As shown in FIG. 2A, a fastening device 17, e.g., hook and loop fasteners, snaps, etc., can be provided to secure a deformable portion 37 of the positioning pad 12 in its undeformed condition after the sheet 16 has been positioned in the transverse cut 36.

In an embodiment, the transverse cut 36 extends from a location spaced from the first end wall 12a through the second end wall 12b. Alternatively, the transverse cut 36 need not extend through the second end wall 12b of the positioning pad 12 but can be spaced from and positioned between the first and second end walls 12a, 12b of the positioning pad 12 or extend through the first end wall 12a of the positioning pad 12 and be spaced from the second end wall 12b.

The tethers 22 are fixedly attached to the positioning pad 12. In the illustrated embodiment, four tethers 22 are secured to the pad 12 with one tether 22 secured at each end of each side wall 12c, 12d of the positioning pad 12. As discussed above, the tethers 22 include a fastening member or members 30, e.g., a buckle or hook and loop fasteners, for securing the tethers to a rail R (FIG. 1) of an operating table T and, thus, fixedly secure the positioning pad 12 to the operating table T.

Referring to FIGS. 1 and 2, in an embodiment, each strap 14 includes a first strap half 14a and a second strap half 14b. One end of each strap half includes a buckle 42 which facilitates securement of the strap half 14 to the rail R of the operating table T. The other end of each strap half 14a, 14b includes a fastening member adapted to engage the fastening member on the other strap half to secure the strap halves 14a, 14b together. In one embodiment, the fastening member includes hook and loop fasteners, e.g., Velcro. Alternately, other fastening members or techniques may be used to secure the strap halves 14a, 14b to each other. In addition, other strap configurations are also envisioned, e. g., the strap can be unitarily formed and attached at each end to the operating table T. Each strap 14 is dimensioned to extend transversely or diagonally across the patient P to secure the patient P to the operating table T as will be discussed in further detail below.

In one embodiment, the patient positioning system 10 includes one or more comfort strips 46 (FIG. 2) which can be positioned between a patient and the strap or straps 14 to prevent patient irritation from the strap 14. In an embodiment, the strips 46 to be positioned between a chest strap 14 (FIG. 4) and a patient P are 34 inches by 6 inches by 2 inches and the strips 46 to be positioned between diagonal straps 14 (FIGS. 1 and 2) and a patient P are 74 inches by 6 inches by 2 inches. The strips 46 can also be positioned between the operating table T and the patient's arms A to more comfortably support the patient P on the operating table T. In an embodiment, these strips are 20 inches by 8 inches by 2 inches. Alternately, comfort strips 46 having a variety of different dimensions are envisioned. The strips 46 can be formed of any suitable material including compressible foam materials or fabrics. Alternately, the use of other materials is envisioned. In an embodiment, the strips 46 have a width which is equal to or larger than the width of the straps 14.

Referring again to FIG. 1, in embodiments, the patient positioning system 10 includes a head rest 50 (FIG. 1). The head rest 50 can include a cylindrical cushion member having an inwardly angled upper wall 52 positioned to support the head of a patient P. Alternately, other head rest configurations are envisioned.

Figure 3:
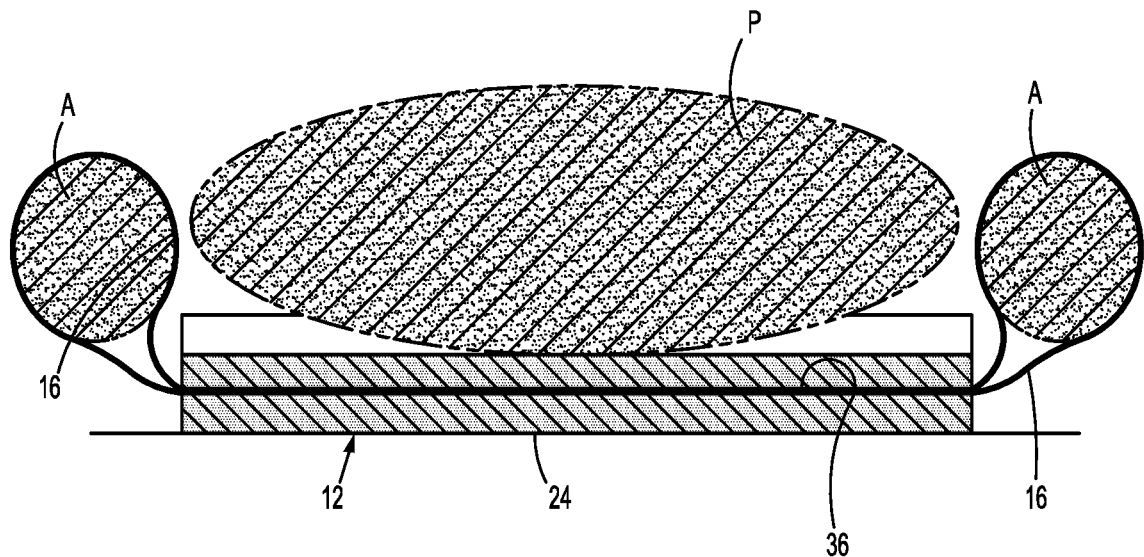
FIG. 3 is a cross-sectional view taken along section line 3-3 of FIG. 1.
Figure 4:
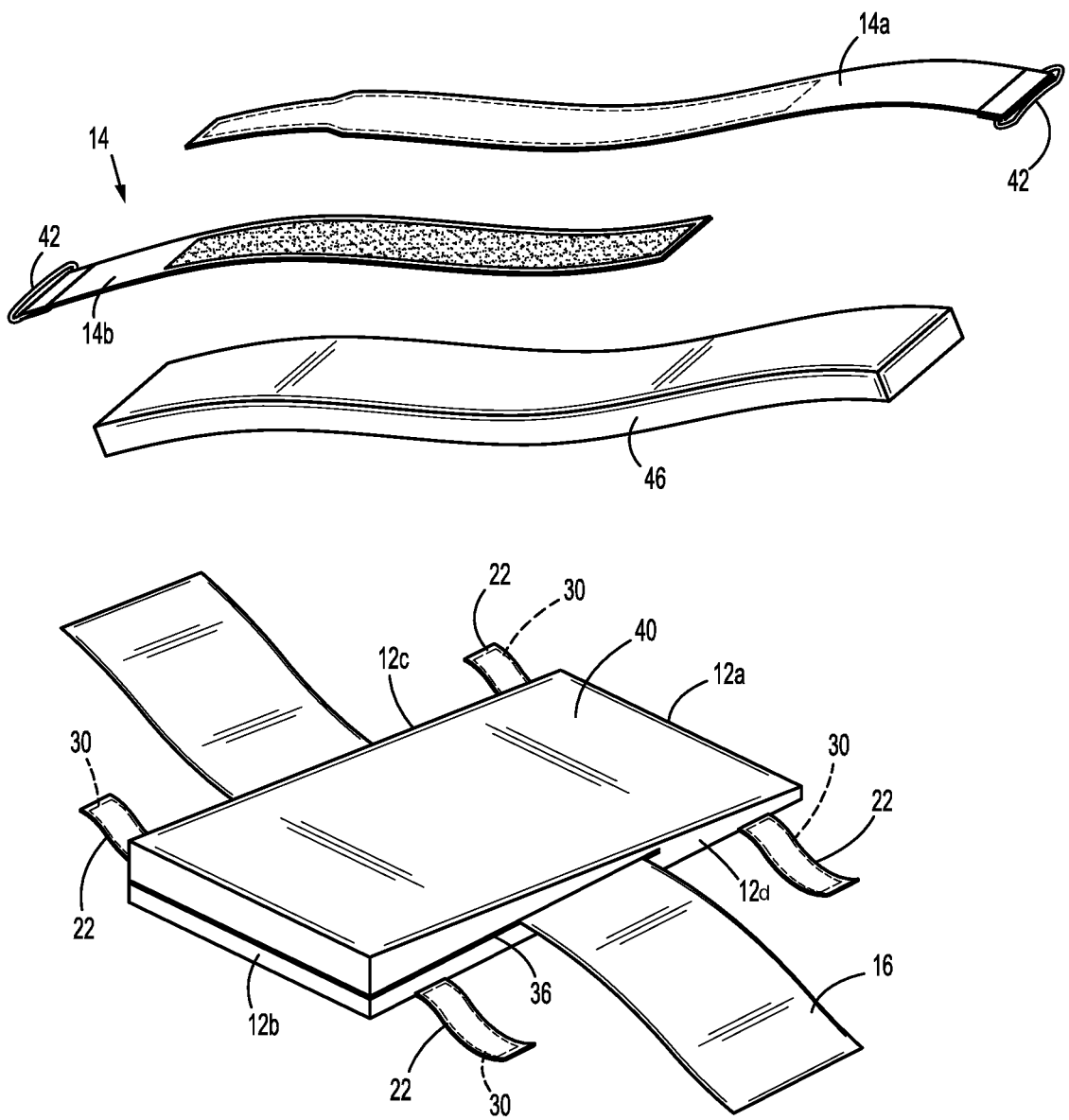
FIG. 4 is another embodiment of the presently disclosed patient positioning system.

In use, the positioning pad 12 is secured to an operating table T using the tethers 22 which are secured to rails R of the operating table T. When securing a patient T in the Trendelenburg position, the table T will be inclined at an angle of between about 15 degrees and 30 degrees. The positioning pad 12 is secured to the table T such that thicker end 12b is positioned below thinner end 12a. Next, the patient P is positioned on the positioning pad 12 with the patient's shoulders positioned on thicker end 12b of the positioning pad 12 and each end of sheet 16 is folded over an arm A (FIG. 3) of the patient P and tucked into the transverse cut 36 of the positioning pad 12. In an embodiment, the sheet 16 is 80 inches by 15 inches. Alternately, it is envisioned that the sheet 16 can have different dimensions to accommodate a particular patient P. After the sheet 16 is positioned about the patient's arms A, the strap(s) 14 can be secured over the patient to secure the patient to the operating table T. In an embodiment shown in FIG. 1, two diagonally positioned straps 14 can be provided to secure the patient P to the operating table T. Alternately, as shown in FIG. 4, a single strap 14 can be used to secure a patient to the operating table T. The single strap 14 can be positioned to extend from one side of the operating table T across the chest of the patient P to the other side of the operating table T. As discussed above, comfort strips 46 can be positioned between the patient P and the straps 14 or between the patient's arms and the operating table T and the patient's arms A to more comfortably support the patient P on the operating table T. In addition, a head rest 50 can be positioned under the patients head.

Figure 5:
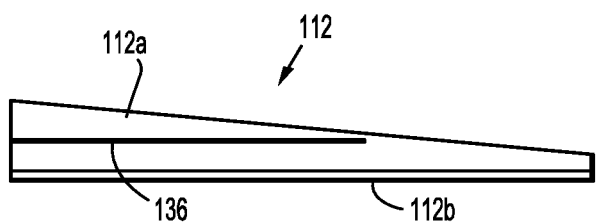
FIG. 5 is a side view of an alternate embodiment of the positioning pad of the presently disclosed patient positioning system.

In an embodiment shown in FIG. 5, the pad 112 is formed from two different compressible materials. A first material layer forms an upper surface 112a of pad 112 which contacts the patient P while a second material layer forms the lower surface 112b of pad 112 which contacts the operating table (not shown). The transverse cut 136 can be formed in the first material layer. In the alternative, the transverse cut 136 can be formed in the second material layer. The first material layer can be a visco-elastic material although the use of other materials is envisioned. The first and second material layers are joined together using, e.g., an adhesive to form a unitary pad 112. In one embodiment, the second material layer has a higher firmness than the first material layer. As such, the second material layer provides structural support to the pad 112 and assists with pressure distribution of the patient on the operating table and the first material layer has the ability to conform or mold to the patient to prevent slippage of a patient P along the pad 112. Both material layers can be tacky to prevent movement of the pad 112 in relation to the operating table and/or the patient. In an embodiment, the second material can be a conventional polyurethane foam and the first material can be a visco-elastic foam. Alternately, a single material having both structural and molding qualities can be used to form the pad. Such a material can also be a conventional polyurethane foam.

In an embodiment, the Indentation Force Deflection (IFD) of the first material can be between about 9 and 15 and the IFD of the second material can be between about 22 and 40. Alternately, first and second materials having wide IFD ranges are envisioned.

Figure 6:
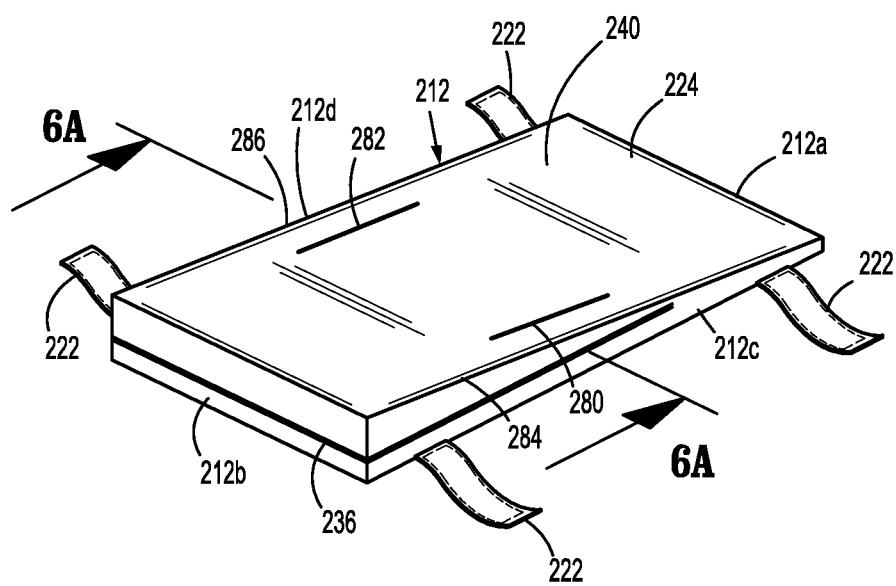
FIG. 6 is a side perspective view of an alternate embodiment of the positioning pad of the presently disclosed patient positioning system.
Figure 6A:
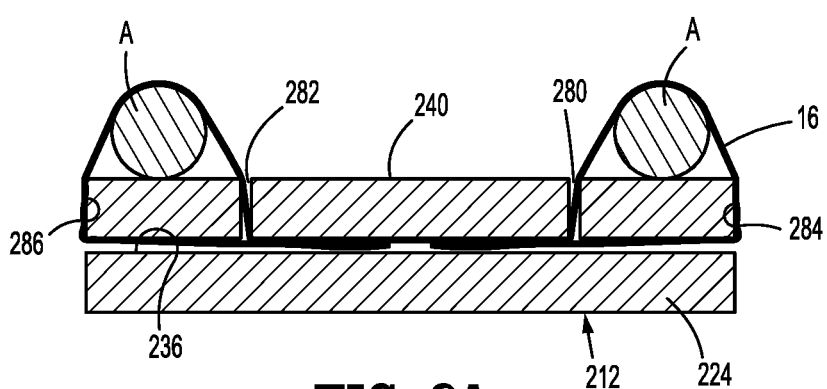
FIG. 6A is a cross-sectional view taken along section line 6A-6A of FIG. 6.

In an alternate embodiment shown in FIGS. 6 and 6A, the positioning pad, shown generally as 212, is substantially the same as positioning pad 12 shown in FIG. 4 and includes a body 224 having a thickness which increases from a first end wall 212a of the positioning pad 212 to a second end wall 212b. The positioning pad 212 is formed from a compressible foam material which defines a slip-resistant or tacky surface 240 and includes a plurality of tethers 222 which are secured to the body 224 at a position to facilitate securement of the positioning pad 212 to an operating table as discussed above. As discussed above with respect to positioning pad 12, positioning pad 212 defines a transverse cut 236 which extends between sidewalls 212c and 212d of body 224 of pad 212. Positioning pad 212 differs from positioning pad 12 in that body 224 defines two additional slits 280 and 282 which are spaced from side edges 284 and 286 of the body 224 and communicate with the transverse cut 236. Slits 280 and 282 facilitate passage of a sheet 16 through a surface of the body 224 and into the transverse cut 236 of the pad 212 at a location spaced from the edges 284 and 286 of the pad 212.

Positioning pad 212 can be used in substantially the same manner as positioning pad 12 as discussed above. In addition, the sheet 16 can be inserted into the slit 280, through the transverse cut 236, and out of slit 282 such that the sheet 16 is positioned on opposite sides of a patient located on the positioning pad 212. Thereafter, each end of the sheet 16 can be wrapped over a patient's arm A and inserted back into the transverse cut 236 to secure the patient to an operating table. As shown in FIG. 6A, when a patient is secured to an operating table using the positioning pad 212, the patient's arms A rest on the tacky surface 240 of the positioning pad 212.

Figure 7:
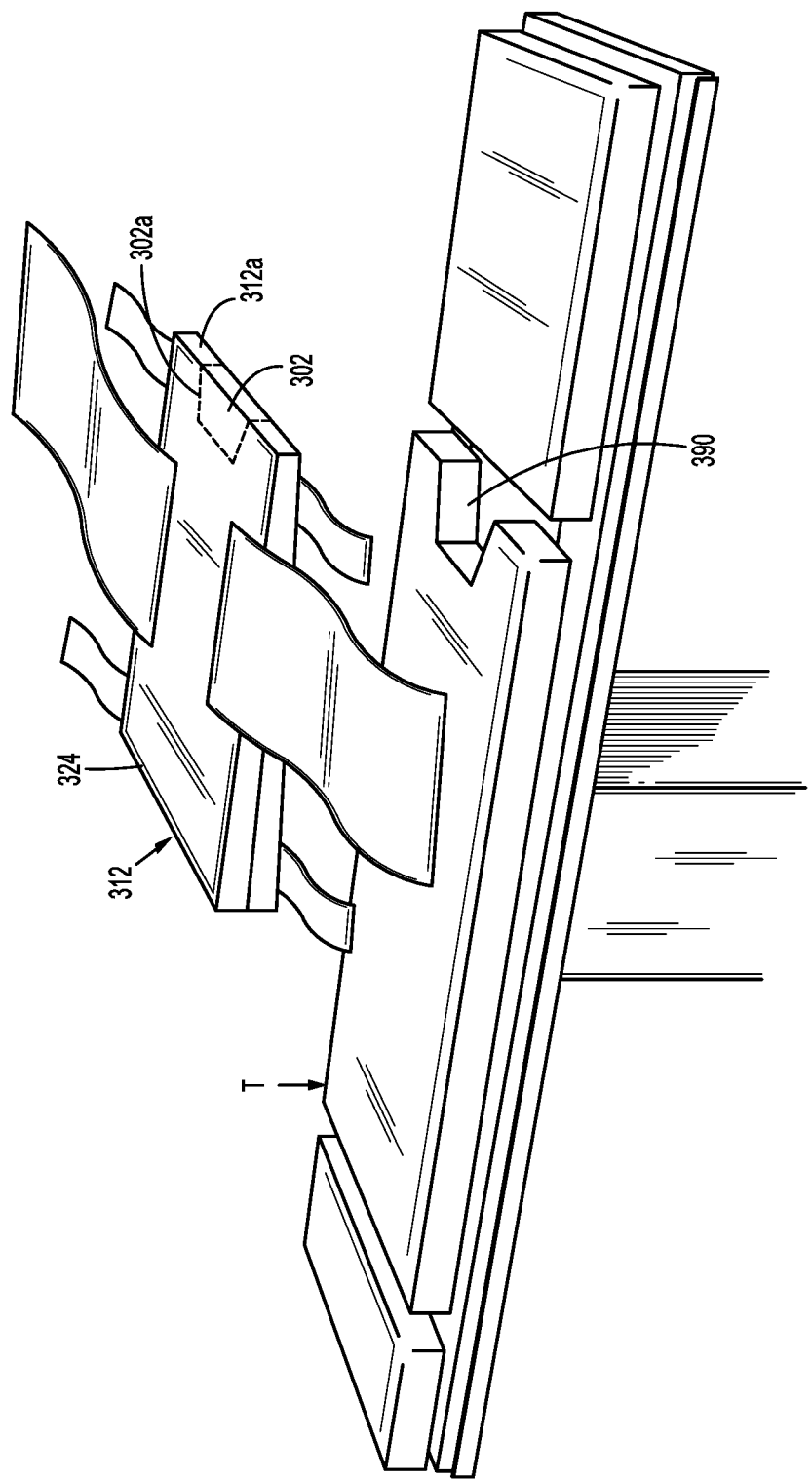
FIG. 7 is a side, perspective view of another embodiment of the positioning pad of the presently disclosed positioning pad system; with a sheet extending through the pad and the pad positioned adjacent an operating table.

FIG. 7 illustrates the presently disclosed positioning pad system including an alternate embodiment of the positioning pad shown generally as 312. Positioning pad 312 is similar to positioning pad 212 shown in FIGS. 6 and 6A, however, in the positioning pad 312, a perforated section 302 defined by a series of perforations 302a is formed adjacent a first end wall 312a of a body 324. The perforated section 302 is configured to mirror the shape of a perineal cutout 390 formed in some operating tables T. Operating or examining tables used for GYN procedures sometimes utilize a perineal cutout 390 in the table T to facilitate access to the perineum. When using the positioning pad 312 on a table T including a perineal cutout 390, the perforated section 302 can be removed from the positioning pad 312 along the series of perforations 302a so as not to obstruct access to the perineal cutout 390 during a surgical procedure.

Figure 8:
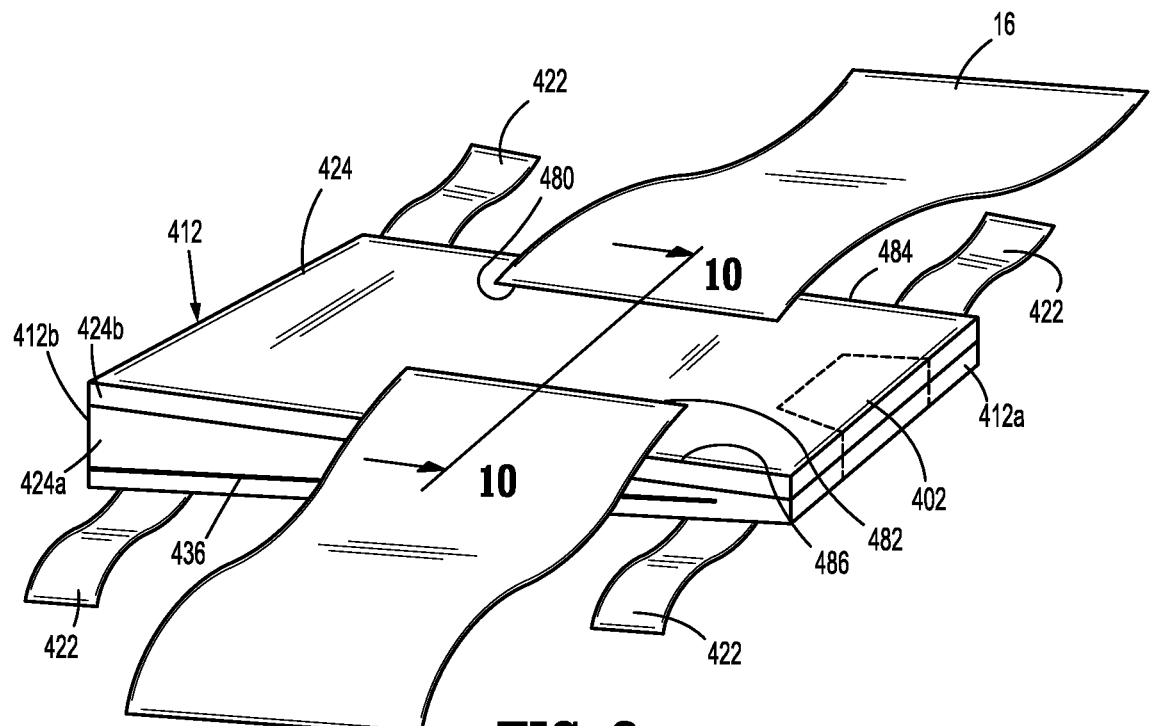
FIG. 8 is a side, perspective view of yet another embodiment of the positioning pad of the presently disclosed positioning pad system with a sheet extending through the pad.
Figure 9:
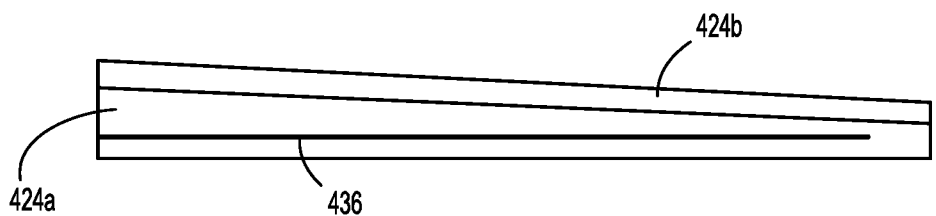
FIG. 9 is a side view of the positioning pad shown in FIG. 8.
Figure 10:
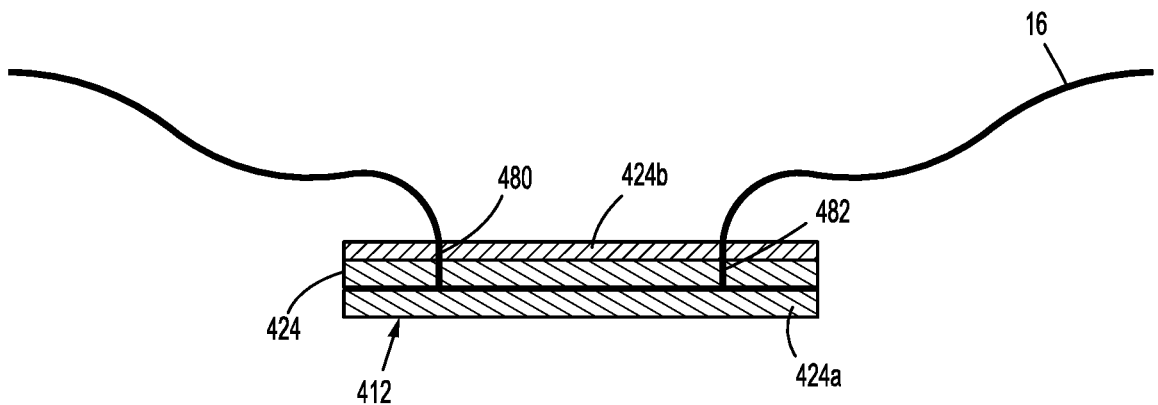
FIG. 10 is a cross-sectional view of the positioning pad and sheet taken along section lines 10-10 of FIG. 8.

FIGS. 8-10 illustrate another embodiment of a positioning pad 412 of the presently disclosed positioning pad system. Positioning pad 412 is similar to positioning pad 312 shown in FIG. 7 and includes a body 424 having a thickness which increases from a first end wall 412a of the positioning pad 412 to a second end wall 412b. The positioning pad 412 includes a plurality of tethers 422 which are secured to the body 424 at a position to facilitate securement of the positioning pad 412 to an operating table. As discussed above, the positioning pad 412 can also define a transverse cut 436, a perforated section 402, and two additional slits 480 and 482 which are spaced from side edges 484 and 486 of the body 424 and communicate with the transverse cut 436. A sheet 16 is provided to pass through slits 480 and 482 and the transverse cut 436 as discussed above with regard to positioning pad 212. Positioning pad 412 differs from positioning pad 312 in that the body 424 of positioning pad 412 is defined by first and second layers 424a and 424b which are bonded together as discussed above with regard to the layers of positioning pad 112.

In embodiments, the first layer 424a is formed of a polyurethane foam, e.g., polyurethane foam grade: RA180-023-450, which has a density of 1.80±0.05 pounds per cubic foot, a 25 percent indentation force deflection (IFD) (four inch thickness) of 23±3 lbf, a minimum resilience (ball rebound) of 45 percent, a minimum tensile strength of 12 psi, a minimum elongation of 125 percent, a minimum tear strength of 1.7 pounds of force per linear inch, and a minimum airflow of 2 cubic feet per minute. In embodiments, the second layer 424b is also formed of a polyurethane foam which is bonded to a top surface of the first layer 424a with an adhesive, such as, for example, SABA Aquabond RSD 3801 in combination with SABA Activator 3739 (each available from SABA Dinxperlo BV, Dinxperlo, the Netherlands). In embodiments, the second layer 424b is a polyurethane foam grade: V450-009-000, which has a minimum density of 4.1 pounds per cubic foot, a 25 percent IFD (four inch thickness) of 9±2 lbf, a minimum tensile strength of 3.5 psi, a minimum elongation of 100 percent, and a minimum airflow of two cubic feet per minute. Alternately, other known deformable materials having the requisite properties can be used to form the first and second layers.

As illustrated, the first layer 424a has a thickness which increases from a first endwall to a second endwall and the transverse cut 436 is formed through the first layer 424a. It is also envisioned that the second layer can have a thickness that increases from a first endwall to a second endwall and that the transverse cut 436 can be formed through the second layer 424. As discussed above with regard to positioning pad 112, layer 424a can have a higher firmness than layer 424b. As such, layer 424b is better able to mold to a patient and layer 424a is better able to provide added support and facilitate improved pressure distribution over the positioning pad 412 onto an operating table. Alternately, layers 424a and 424b can be formed of materials having a variety of different characteristics. The positioning pad 412 is used in the same manner as the positioning pad 212 and will not be described in further detail herein.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A positioning pad for positioning a patient on an operating table comprising:
   a body formed from a compressible material having a slip-resistant surface and having a first end, a second end, a first side wall, and second side wall, the body having a thickness which increases from the first end of the body to the second end of the body; and
   a plurality of tethers, a first of the plurality of tethers fixedly secured to the body and extending from the first side wall and a second of the plurality of tethers secured to the body and extending from the second side wall, each of the tethers including a fastening member adapted to secure the body to the operating table.

2. The positioning pad of claim 1, wherein the body includes a transverse cut which extends transversely from the first side wall of the body to the second side wall of the body and through the first side wall and the second side wall, the transverse cut being configured to allow placement of a sheet through the positioning pad in spaced relation to the slip-resistant surface.

3. The positioning pad of claim 2, wherein the fastening member of each of the tethers includes hook and loop fasteners.

4. The positioning pad of claim 2, wherein the thickness of the body at the first end is one inch and the thickness of the body at the second end is three inches.

5. A positioning pad for positioning a patient on an operating table comprising:
   a body formed from a compressible material having a slip-resistant surface, a first end and a second end, the body having a thickness which increases from the first end of the body to the second end of the body; and
   a plurality of tethers fixedly secured to the body, each of the tethers including a fastening member adapted to secure the body to the operating table,
   wherein the body includes a transverse cut which extends transversely from one side wall of the body to an opposite side wall of the body, the transverse cut being configured to allow placement of a sheet through the positioning pad in spaced relation to the slip-resistant surface, and wherein the transverse cut is spaced from the first end of the body and extends through the second end of the body.

6. The positioning pad of claim 5, wherein the fastening member of each of the tethers includes hook and loop fasteners.

7. The positioning pad of claim 5, wherein the body is formed from first and second layers bonded together.

8. The positioning pad of claim 7, wherein the first and second layers are formed of polyurethane foams.

9. The positioning pad of claim 2, wherein the transverse cut is spaced from the first end of the body and extends through the second end of the body.

10. The positioning pad of claim 1, wherein the body is formed from first and second layers bonded together.

11. The positioning pad of claim 10, wherein the first and second layers are formed of polyurethane foams.

* * * * *